US00PP22209P2

(12) United States Plant Patent
Farrow

(10) Patent No.: US PP22,209 P2
(45) Date of Patent: Oct. 25, 2011

(54) ***RHODODENDRON* PLANT NAMED 'FARROW'**

(50) Latin Name: *Rhododendron hybrida*
Varietal Denomination: Farrow

(75) Inventor: Michael W. Farrow, Earleville, MD (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,831

(22) Filed: Sep. 14, 2010

(51) Int. Cl.
*A01H 5/00* (2006.01)
(52) U.S. Cl. ..... Plt./238
(58) Field of Classification Search ..... Plt./238
See application file for complete search history.

*Primary Examiner* — Kent L Bell
(74) *Attorney, Agent, or Firm* — C. A. Whealy

(57) ABSTRACT

A new and distinct cultivar of *Rhododendron* plant named 'Farrow', characterized by its compact, upright, somewhat outwardly spreading and mounding plant habit; freely branching habit; dense and bushy plant form; glossy green and pale yellow variegated leaves; freely flowering habit; large single type red purple-colored flowers; and good garden performance.

2 Drawing Sheets

Botanical designation: *Rhododendron hybrida.*
Cultivar denomination: 'FARROW'.

BACKGROUND OF THE INVENTION

The present Invention relates to a new and distinct cultivar of *Rhododendron* plant, botanically known as *Rhododendron hybrida* and hereinafter referred to by the name 'Farrow'.

The new *Rhododendron* plant is a naturally-occurring branch mutation of *Rhododendron hybrida* 'Silver Sword', not patented. The new *Rhododendron* plant was discovered and selected by the Inventor on a single flowering plant of 'Silver Sword' in an outdoor nursery in Earleville, Md. during the summer of 2001.

Asexual reproduction of the new *Rhododendron* plant by softwood cuttings taken in a controlled environment in Earleville, Md. since 2001 has shown that the unique features of this new *Rhododendron* plant are stable and reproduced true to type in successive generations.

SUMMARY OF THE INVENTION

Plants of the new *Rhododendron* have not been observed under all possible environmental conditions. The phenotype may vary somewhat with variations in environment such as temperature and light intensity without, however, any variance in genotype. The following traits have been repeatedly observed and are determined to be the unique characteristics of 'Farrow'. These characteristics in combination distinguish 'Farrow' as a new and distinct *Rhododendron* plant:

1. Compact, upright, somewhat outwardly spreading and mounding plant habit.
2. Freely branching habit, dense and bushy plant form.
3. Glossy green and pale yellow variegated leaves.
4. Freely flowering habit.
5. Large single type red purple-colored flowers.
6. Good garden performance.

Plants of the new *Rhododendron* differ primarily from plants of the female parent, 'Silver Sword', in the following characteristics:

1. Plants of the new *Rhododendron* have glossier leaves than plants of 'Silver Sword'.
2. Leaves of plants of the new *Rhododendron* have a wider white-colored border than leaves of plants of 'Silver Sword'.
3. Plants of the new *Rhododendron* and 'Silver Sword' differed slightly in flower color.

Plants of the new *Rhododendron* can be compared to the plants of 'Girard's Rose', not patented. In side-by-side comparisons plants of the new *Rhododendron* differ primarily from plants of 'Girard's Rose' in the leaf coloration as plants of 'Girard's Rose' have solid green-colored leaves.

BRIEF DESCRIPTION OF THE PHOTOGRAPHS

The accompanying colored photographs illustrate the overall appearance of the new *Rhododendron* plant. These photographs show the colors as true as it is reasonably possible to obtain in colored reproductions of this type.

Colors in the photographs may differ slightly from the color values cited in the detailed botanical description which accurately describe the colors of the new *Rhododendron* plant.

The photograph on the first sheet comprises a side perspective view of a typical flowering plant of 'Farrow' grown in a container.

The photograph on the second sheet is a close-up view of a typical flowering plant of 'Farrow'.

DETAILED BOTANICAL DESCRIPTION

The aforementioned photographs and following observations and measurements describe plants grown during the spring and summer in an outdoor nursery in Grand Haven, Mich. and under commercial *Rhododendron* production conditions. Plants were four years old when the photographs and description were taken. In the following description, color references are made to The Royal Horticultural Society Colour Chart, 2001 Edition, except where general terms of ordinary dictionary significance are used.

Botanical classification: *Rhododendron hybrida* 'Farrow'.

Parentage: Naturally-occurring branch mutation of *Rhododendron hybrida* 'Silver Sword', not patented Propagation:

*Type.*—By softwood cuttings.

*Time to initiate roots, summer.*—About 40 days at temperatures of about 34° C.

*Time to produce a rooted young plant, summer.*—About four months at temperatures of about 34° C.

*Root description.*—Fine, fibrous; white in color.

*Rooting habit.*—Freely branching, dense.

Plant description:

*Plant form and growth habit.*—Perennial and evergreen flowering shrub; compact, upright, somewhat outwardly spreading and mounding plant habit; freely branching habit; dense and bushy plant form; vigorous growth habit; freely flowering habit with numerous showy single type flowers.

*Branching habit.*—Freely branching habit with about 57 lateral branches developing per plant; pinching (removal of terminal apex) enhances lateral branch development.

*Plant height.*—About 50 cm.

*Plant diameter, area of spread.*—About 35 cm.

*Lateral branch description.*—Length: About 11 cm. Diameter at base: About 2 mm. Internode length: About 1 cm. Strength: Strong. Aspect: About 20° to 30° from vertical. Texture, developing: Pubescent. Texture, mature: Pubescent, woody. Color, developing: Close to 144B. Color, developed: Close to 165A.

*Foliage description.*—Arrangement: Alternate or whorled; simple. Length: About 4 cm. Width: About 1.5 cm. Shape: Lanceolate to oblanceolate. Apex: Acute. Base: Cuneate to attenuate. Margin: Entire; undulate. Venation pattern: Pinnate; reticulate. Texture, upper surface: Smooth, glabrous. Texture, lower surface: Slightly pubescent. Luster: Glossy. Color: Developing leaves, upper and lower surfaces: Center, close to 146B; towards the margins, close to 10D. Fully expanded leaves, upper surface: Center, close to 146A; towards the margins, close to 11D; venation, similar to leaf surface coloration. Fully expanded leaves, lower surface: Center, close to 146B; towards the margins, close to 11D; venation, similar to leaf surface coloration. Petiole: Length: About 1 cm. Diameter: About 1 mm. Texture, upper and lower surfaces: Pubescent. Color, upper and lower surfaces: Close to 146C.

Flower description:

*Flower arrangement and appearance.*—Single type flowers arranged in clusters with usually about two to five flowers per lateral stem; freely flowering habit with about 187 flowers per plant; flowers face upward or outwardly; flowers rotate with a single whorl of five petals.

*Natural flowering season.*—Plants flower in May in Grand Haven, Mich.

*Flower longevity.*—Durable and long-lasting; flowers last about three to five weeks on the plant; flowers not persistent.

*Fragrance.*—None detected.

*Flower diameter.*—About 6 cm.

*Flower depth.*—About 4.4 cm.

*Petals.*—Arrangement: Single whorl of five petals fused at the base forming a wide funnel-shaped corolla. Length: About 2.5 cm. Width: About 1.5 cm to 2 cm. Lobe shape: Ovate. Apex: Acute; undulate and ruffled. Margin: Entire; undulate and ruffled. Texture, upper and lower surfaces: Smooth, glabrous. Color: When opening, upper and lower surfaces: Close to 57A. Fully opened, upper and lower surfaces: Close to 57A.

*Sepals.*—Arrangement: Five in a single whorl, fused at the base forming a star-shaped corona. Length: About 9 mm. Width: About 3 mm. Shape: Lanceolate. Apex: Narrowly acute. Base: Fused. Margin: Entire. Texture, upper and lower surfaces: Pubescent. Color, upper and lower surfaces: Close to 145D.

*Peduncles.*—Length: About 1.2 cm. Diameter: About 2 mm. Angle: Mostly upright. Strength: Strong. Texture: Pubescent. Color: Close to 145D tinged with close to 57A.

*Reproductive organs.*—Androecium: Quantity of stamens per flower: About five. Anther shape: Rounded. Anther length: Less than 1 mm. Anther color: Close to 57A. Pollen amount: Scarce. Pollen color: Close to 57A. Gynoecium: Pistil length: About 3.2 cm. Stigma shape: Rounded. Stigma color: Close to 57A. Style length: About 3 cm. Style color: Close to 57A. Ovary color: Close to 155C.

*Seeds.*—Quantity per fruit: Numerous. Length: Less than 1 mm. Diameter: Less than 1 mm. Color: Brown.

Garden performance: Plants of the new *Rhododendron* have been observed to have good garden performance and to be tolerant to rain, wind and temperatures ranging from about −24° C. to about 36° C.

Disease/pest resistance: Plants have not been observed to be resistant to pathogens and pests common to *Rhododendrons*.

It is claimed:

1. A new and distinct cultivar of *Rhododendron* plant named 'Farrow' as illustrated and described.

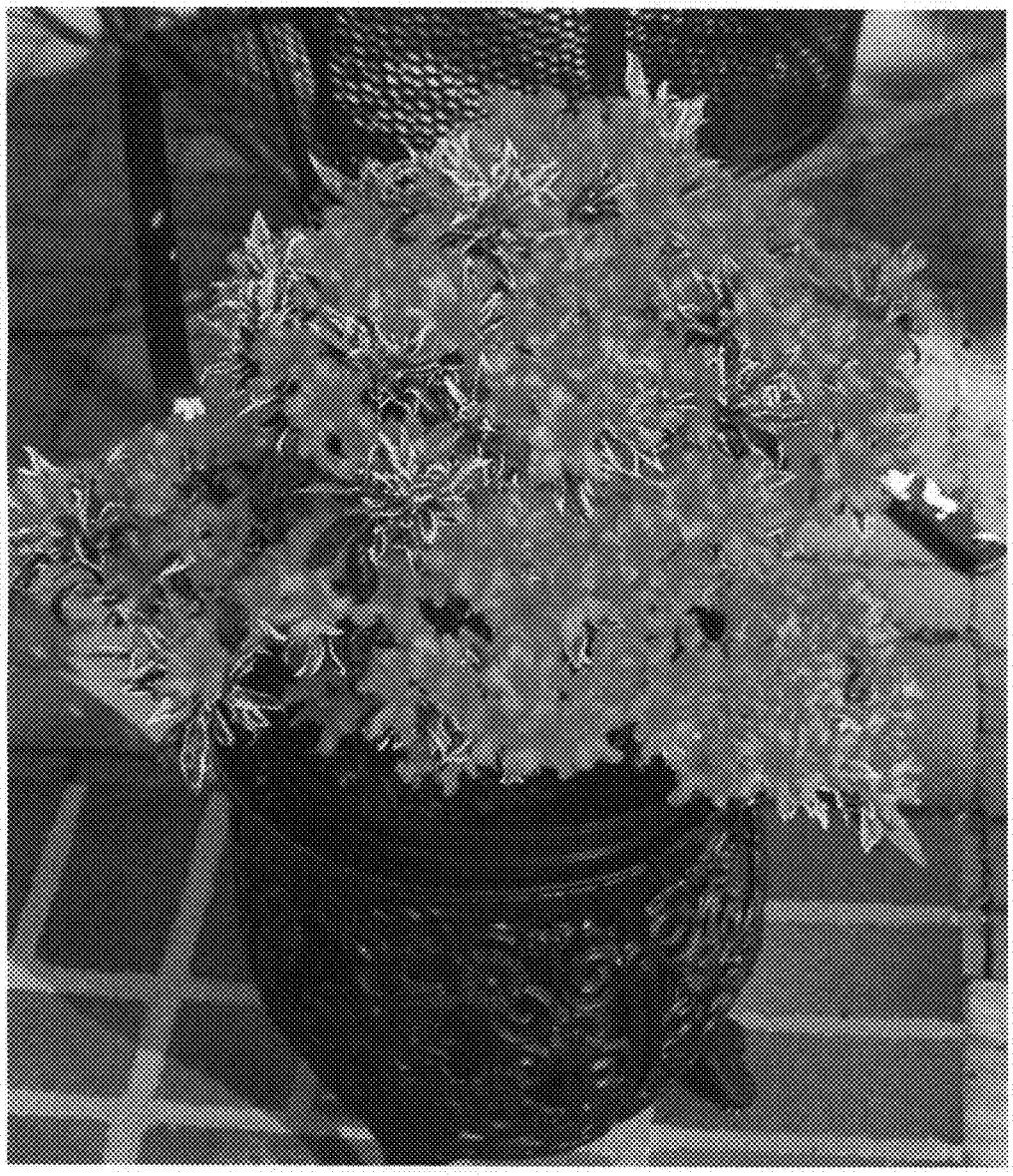

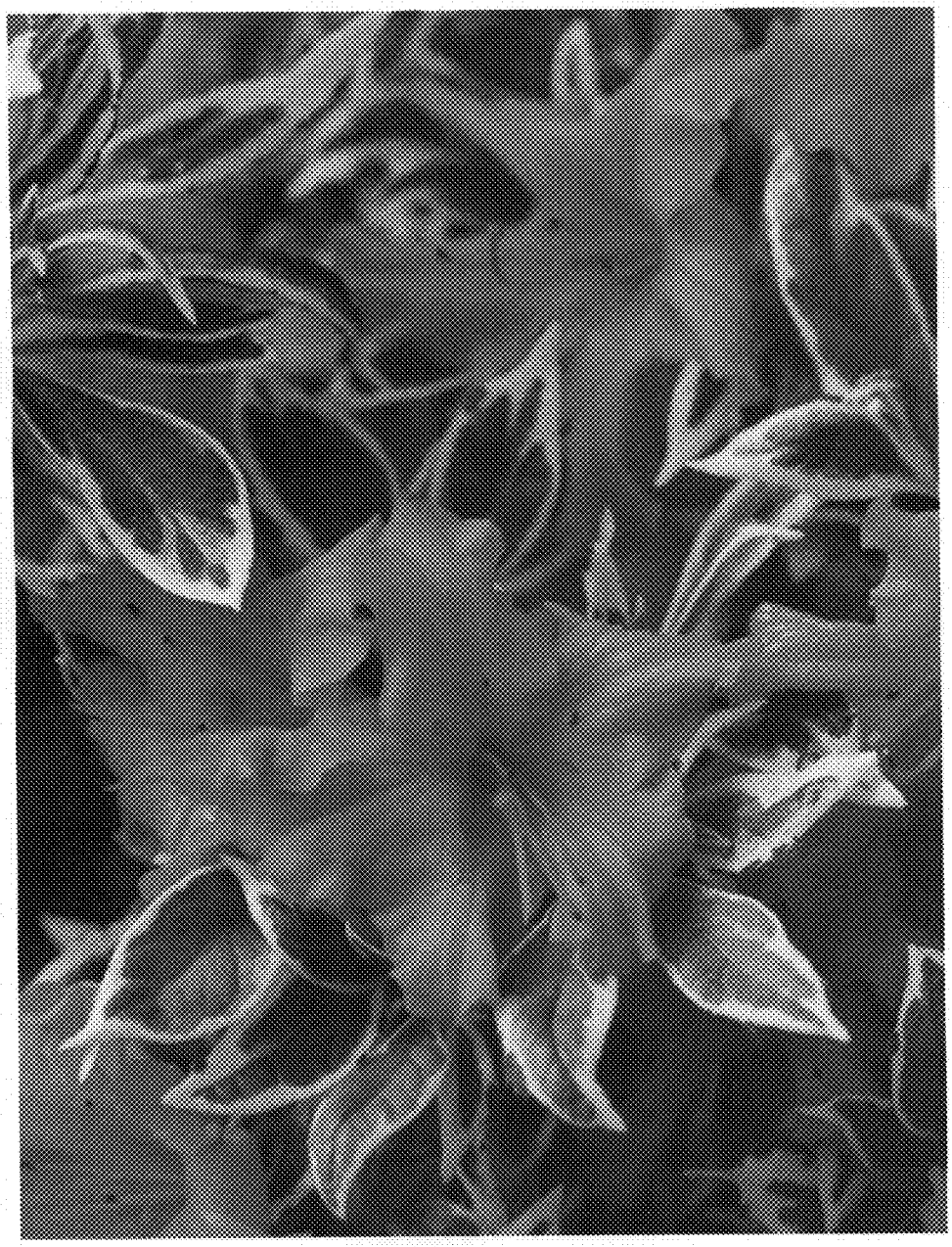

* * * * *